United States Patent [19]
Ellis et al.

[11] Patent Number: 5,817,881
[45] Date of Patent: Oct. 6, 1998

[54] TETRAALYKYLAMMONIUM POLYOXOANIONIC OXIDATION CATALYSTS

[75] Inventors: Paul E. Ellis, Downingtown; James E. Lyons, Wallingford; Harry K. Myers, Jr., Cochranville; Shahid N. Shaikh, Media, all of Pa.

[73] Assignee: Sun Company, Inc. (R&M), Philadelphia, Pa.

[21] Appl. No.: 902,931

[22] Filed: Jul. 30, 1997

[51] Int. Cl.$^6$ .................................................... C07C 45/33
[52] U.S. Cl. ........................ 568/399; 568/398.8; 568/910; 568/910.5
[58] Field of Search .................................... 568/394, 399, 568/398.8, 910, 910.5

[56] References Cited

U.S. PATENT DOCUMENTS

| | | | |
|---|---|---|---|
| 4,803,187 | 2/1989 | Lyons et al. | 502/200 |
| 4,859,798 | 8/1989 | Lyons et al. | 569/399 |
| 4,864,041 | 9/1989 | Hill | 568/399 |
| 4,898,989 | 2/1990 | Ellis et al. | 568/399 |
| 5,091,354 | 2/1992 | Ellis et al. | 568/399 |

OTHER PUBLICATIONS

Toth, J.E., Doctoral Dissertation, "Electrocatalytic Activity of Transition Metal Substituted Heteropolytungstates", *California Institute of Technology, Pasadena, California pp. 28–29, (1990)*.

Lyons, et al., *Structure —Activity and Selectivity Relationships in Heterogeneous Catalysis*, "Active Iron Oxo Centers for the Selective Catalytic Oxidation of Alkanes", *Elsevier Science Publishers B. V. Amsterdam pp. 99–116, 1991*.

Pope, et al., Hetropoly and Isopoly Oxometalates, *Springer–Verlag pp. 17–18, New York (1993)*.

Ai, M., "Partial Oxidation of n–Butane with Heteropoly Compound–based catalysts", *Lobo. Resources Utiliz., Tokyo Inst. Tech., Yokohama, Japan, pp. v–475–v486*.

*Primary Examiner*—James H. Reamer
*Attorney, Agent, or Firm*—Stephen T. Falk, Esq.

[57] ABSTRACT

Alkanes are catalytically oxidized in air or oxygen using iron-substituted polyoxoanions (POAs) of the formula:

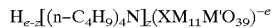

$$H_{e-f}[(n-C_4H_9)_4N]_f(XM_{11}M'O_{39})^{-e}$$

The M' (e.g., iron(III)/iron(II)) reduction potential of the POAs is affected by selection of the central atom X and the framework metal M, and by the number of tetrabutylammonium groups. Decreased Fe(III)/Fe(II) reduction potential has been found to correlate to increased oxidation activity.

20 Claims, No Drawings

TETRAALYKYLAMMONIUM POLYOXOANIONIC OXIDATION CATALYSTS

The Government of the United States of America has rights in this invention pursuant to Cooperative Agreement No. DE-FC21-90MC26029 awarded by the U.S. Department of Energy.

FIELD OF THE INVENTION

This invention relates to the oxidation of alkanes with iron-substituted polyoxoanions (POAs). Selection of the central atom, framework elements and number of tetraalkyl-ammonium groups affects the activity of the catalyst.

BACKGROUND OF THE INVENTION

The use of HPAs and POAs for the catalytic oxidation of alkanes in air and in liquid phase is known. See, for example, Ai, "Partial Oxidation of n-Butane with Heteropoly Compound-based Catalysts", *Proceedings of the 8th International Congress on Catalysis*, Berlin, 1984, Verlag Chemie, 5, 475; Lyons et al., U.S. Pat. No. 4,803,187; Lyons, et al., U.S. Pat. No. 4,859,798; Ellis et al., U.S. Pat. No. 4,898,989; Ellis et al., U.S. Pat. No. 5,091,354; Lyons et al., *Studies in Surface Science and Catalysis*, 67, 99–116 (1991).

HPAs and POAs and their preparation are described in Pope et al., *Heteropoly and Isopoly Oxo-metalates*, Springer-Verlag, N.Y. (1983). In order to clarify terminology used in the art, consider first a specific precursor of the compositions used in the present invention: $H_3PW_{12}O_{40}$. Since the cations in this material are hydrogen, the compound is referred to as a heteropolyacid. If the cations are not hydrogen, but are metals such as an alkali metal, potassium, sodium or lithium, or are ammonium or alkylammonium, as in $K_3PW_{12}O_{40}$ or $(NH_4)_3PW_{12}O_{40}$, then it is no longer an acid, and is referred to as a polyoxoanion (POA).

As described in Pope et al., HPAs and POAs are cage-like structures with a primary, generally centrally located atom (s) surrounded by the cage framework which contains a plurality of other metal atoms, the same or different, bonded to oxygen atoms. Since the central metal atom is different from the other atoms, it is described as "hetero". The other metal atoms are transition metals and have oxygen bonding such as:

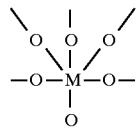

As disclosed in Lyons et al., U.S. Pat. No. 4,859,798, conventional HPAs and POAs may be promoted by the substitution of certain metals in the framework of the HPA or POA with certain other metal atoms. Ellis et al., U.S. Pat. No. 4,898,989, discloses a type of framework substitution wherein three metal atoms in a single triangular face in the HPA/POA framework are replaced with three different metal atoms, thereby enhancing catalytic activity.

Hill, U.S. Pat. No. 4,864,041, discloses use of polyoxoanion quartenary salts as catalysts for the oxidation of a broad range of organic compounds in the presence of an oxygen-donor, such as iodosylbenzene.

J.E. Toth, Doctoral Dissertation, entitled "Electrocatalytic Activity of Transition Metal Substituted Heteropolytungstates," California Institute of Technology, Pasadena, Calif. (1990), has reported that the iron(III)/iron (II) reduction potential of iron in Keggin ion complexes is dependent on the nature of the central heteroatom of the POA. The reduction potential was found to increase as the central atom was varied in the order: $Si^V > Ge^{IV} > P^V > As^V$. Over that series, the $Fe^{III}/Fe^{II}$ reduction potential varies over a span of nearly 270 mV from −0.145 mV to +0.123 mV.

SUMMARY OF THE INVENTION

The invention involves an improved method of catalytic air oxidation of alkanes using polyoxoanions. Alkanes are catalytically oxidized using iron-substituted POAs of the formula:

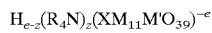

The M' (e.g., iron(III)/iron(II)) reduction potential of the POAs is affected by selection of the central atom, X, the selection of the framework metal, M, and by the number of tetraalkyl-ammonium groups, z (R is alkyl group with 1 to 8 carbon atoms). Decreased M' (e.g., $Fe^{III}/Fe^{II}$) reduction potential correlates to increased oxidation activity.

An advantage of the process of the present invention is that the catalyst used are soluble in organic solvents, such as acetonitrile, benzonitrile and acetic acid. A further advantage of the present invention is that, if under reaction conditions pyrolysis occurs leading to H+ incorporation, the resulting composition remains an active oxidation catalyst. Another feature of the catalysts used in the process of the invention is that they can have textural modifying properties; i.e., the tetraalkylammonium groups occupy space in the formation of the solid catalyst and if such groups are removed by pyrolysis voids can be formed which introduce porosity to the catalyst.

DETAILED DESCRIPTION OF THE INVENTION

The invention comprises a method of catalytic air oxidation of hydrocarbon employing polyoxoanions as catalysts. The POAs useful in the invention have the general Keggin formula:

$$[H_{e-z}(R_4N)_z](XM_{11}M'O_{39})^{-e}$$

or Dawson formula:

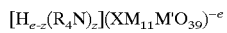

where the central atom X comprises one or two elements selected from the group consisting of Group IIIB–VIB elements; M comprises molybdenum, tungsten or vanadium or combinations thereof, and M' is ruthenium or first row transition metal substituted in the framework for a metal-oxygen (M=O) unit in the framework. R is an alkyl group with one to eight carbons atoms. The notation "e" is the charge on the $(XM_{11}M'O_{39})$ or $(X_2M_{17}M'O_{61})$ group and will vary from case to case; however, "e" is always the sum of the number of hydrogen atoms (e−z) and tetraalkylammonium groups (z) needed to electronically balance the formula. The process of the invention involves oxidation in air or $O_2$ without the use of so-called oxygen-donors, such as iodosylbenzene.

The process of the invention is more generally a method for oxidation of alkanes which comprises contacting alkane in the presence of air or oxygen with a catalyst comprising a tetraalkylammonium polyoxoanion. The POA comprises (a) one or two central atoms (X) selected from the group consisting of Group IIIA–VIA elements of the Periodic Table; (b) a framework comprising 17 to 61 oxygen atoms (O) and 4 to 19 framework metal atoms (M) selected from the group consisting of molybdenum, tungsten and vanadium and combinations thereof, (c) one or more atoms (M') selected from the group consisting of ruthenium and first row transition metals substituted for one or more framework metal-oxygen units (M=O) in the framework; and (d) a sufficient number (e) of cations to electronically balance the charge (–e) of said polyoxoanion, wherein at least one of said cations comprises tetraalkylammonium cation. These POAs may be of the Keggin or Dawson structures. Where there are more than one M' atom substituted for M=O units in the framework, the M' may be randomly substituted or geometrically controlled substitutions. These POAs may be prepared according to the method taught by Ellis et al. U.S. Pat. No. 5,091,354.

In the catalysts useful in the present invention, the central atom X is preferably one atom, but may be two atoms, from Group IIIB, Group IVB, Group VB or Group VIB elements of the Periodic Table. Among these elements, phosphorus, antimony, silicon, boron are preferred; phosphorus being most preferred. The metal M is molybdenum, tungsten or vanadium or combinations thereof Ruthenium or first row transition metals are substituted for a metal-oxygen unit (M=O) in the framework; preferably, such M' atoms are iron, chromium or ruthenium.

The POAs useful in the present invention comprise tetraalkylammonium ($R_4N^+$) organic cations associated with the metal framework. Preferred cations include tetrabutylammonium [$(n-C_4H_9)_4N$], however, R may be other alkyl groups, for example $C_1$ to $C_8$ alkyl groups. The number of hydrogen atoms and tetraalkylammonium groups (e) varies according to the charge (–e) on the metal framework moiety; for the $(XM_{11}M'O_{3g})^{-e}$ moiety, e varies from 4 to 6. Preferred Keggin type catalysts for use in the present invention contain four tetraalkylammonium groups and zero to two hydrogen atoms. The sum of the number of hydrogen atoms and the number of tetraalkylammonium groups always equals e. For Dawson type structures, the charge on the $(X_2M_{17}M'O_{61})^{-e}$ moiety is higher, generally up to 10, due to the overall charge on the anion resulting in a greater number of cations to balance the charge. The number can be readily determined for any given framework formula.

The M' framework-substituted POAs may be further promoted with azide; for example, the sodium azide POA: $[(nC_4H_9)_4N]_4(PW_{11}FeO_{39})\cdot NaN_3$.

The POAs may be prepared in the manner known in the art. The procedures therefor described in Lyons et al., U.S. Pat. No. 4,803,187; Ellis et al., U.S. Pat. No. 4,898,989; and Ellis et al., U.S. Pat. No. 5,091,354, are applicable and are hereby incorporated by reference herein.

The catalysts can be used for vapor phase oxidation of alkanes as well as liquid phase operation. In the former instance, the alkane is mixed with an oxygen-containing gas and is contacted with the catalyst, typically in a packed bed reactor. For both vapor and liquid phase operation, the process may be carried out in any conventional reactor configuration.

The oxidation is carried out in liquid phase at 50 to 200° C., preferably 50 to 150° C.; low temperature is an advantage of the invention. The low temperature liquid phase process is made possible in part by the increased solubility of the catalyst due to the presence of the tetraalkylammonium groups. The pressure is 0 to 5000 psig, preferably 15 to 1500 psig. Reaction time is 0.1 to 20 hours depending on the conditions and is readily selected by the skilled worker.

Vapor phase oxidation is carried out at 150 to 400° C. The pressure is 15 to 1200 psig, preferably 15 to 100 psig. The amount of catalyst employed is generally 0.0001 to 1.0 mmoles catalyst per mole of reactant, preferably 0.0001 to 0.1, but is always a catalytically effective amount.

The alkane starting materials include straight and branched-chain compounds having from about 1 to 20 carbon atoms, preferably 1 to 5, such as methane, ethane, propane, n-butane, isobutane, n-pentane, n-hexane, 2-methylpentane, 3-methylpentane, heptane, 2-methylheptane, 3-methylheptane and the like, as well as cycloalkanes having from about 5 to 20 carbon atoms, preferably 5 to 10 carbon atoms, such as cyclopentane, cyclohexane, cycloheptane, cyclooctane and the like. These compounds, if desired, may be substituted with various moieties, although care should be taken to exclude substituents which will adversely affect the activity of the catalyst.

The process is highly selective for producing alcohols and ketones, selectivity being defined as a mole percentage of the alkane reacted which is converted to the desired product. In liquid phase, the selectivity to alcohol is usually over 40%, often over 60%, and in some cases over 80%. The selectivity to alcohol and ketone is usually over 90%, frequently over 95%, a truly outstanding result. Small amounts of acids are sometimes formed. The amount of carbon oxides formed is generally under 10%, usually less than 5% and is often under 2%, the percentages being expressed as the mole percent yield of carbon oxides based on the reacted alkane.

The M' (e.g., iron$^{(III)}$/iron$^{(II)}$) reduction potential of the catalysts useful in the present invention was studied to evaluate the relationship between the reduction potential and the oxidation activity of the catalysts. The $Fe^{III}/Fe^{II}$ reduction potential was manipulated by varying (1) the central atom X in the POA, (2) the framework metal M in the POA, and (3) the number of tetraalkylammonium ligands in the POA complex.

The electrochemical studies were performed using EG&G Princeton Applied Research (PAR) Model 273 instrumentation using Model 270 Electrochemical Analysis Software. Each POA complex was dissolved in 0.1 M tetrabutylammonium hexafluorophosphate ($TBAPF_6$) in $CH_3CN$ to a concentration of 2.0 mM and then acetate buffer was added to pH 4.7. Scan rates were kept constant at 200 mV/s. A coil of platinum wire served as the counter electrode. BAS glassy carbon electrode and Ag/AgCl were used as working and reference electrodes, respectively. Between each run, the solutions were purged with $N_2$ for at least five minutes. The $E_{1/2}$ for the ferrocene/ferrocene+($Fc/Fc^+$) couple under the above conditions was 283 mV.

Example 1

The effect of the central heteroatom X on the $Fe^{III}/Fe^{II}$ reduction potential and oxidation activity of heteroatom-tungstates was studied. The catalyst complexes were of the formula:

$$H_{e-4}[n-C_4H_9)_4N]_4(XW_{11}FeO_{39})^{-e}$$

where X is boron, silicon, phosphorus, arsenic, bismuth, germanium and antimony and "e" is four to six. The reduction potentials were examined by cyclic voltametry of either the corresponding potassium salts in water or the tetrabutylammonium salts in acetonitrile. Both solutions contained buffers. The oxidation reactions were performed under the conditions described in Table I. The data set forth in Table I show the general direct relationship between increased $Fe^{III}/Fe^{II}$ reduction potential and oxidation activity.

Example 2

The effect of the number of tetrabutylammonium groups on the oxidation activity of iron-substituted silico-and phosphotungstates was studied. Oxidation activity was determined in relation to low temperature, liquid phase oxidation of propane. The oxidation reactions were performed under the conditions described in Table II. As the data in Table II show, addition of the fourth tetrabutylammonium group is associated with a decrease in catalytic activity.

Example 3

The effect of the framework metal M on the oxidation activity of iron-substituted POAs was studied by comparing the activity of two pairs of iron-substituted complexes. One pair consisted of an iron-substituted silicotungstate and an iron-substituted silicomolybdate. The second pair consisted of an iron-substituted phosphotungstate and an iron-substituted phosphomolybdate. The oxidation reactions were performed under the conditions described in Table III. The results in Table III show that the tungsten-containing complexes had slightly higher activity.

TABLE I

EFFECT OF THE CENTRAL HETEROATOM, X, ON PROPANE OXIDATIONS CATALYZED BY KEGGIN CATALYSTS[a]

| CATALYST | $X^{(A)}$ A | Charge on Complex, Z | $Fe^{III}/Fe^{II}$, $E_{1/2}$, $V^b$ | TO | ONE/ OL[c] |
|---|---|---|---|---|---|
| $[BW_{11}Fe(H_2O)O_{39}][(n-C_4H_9)_4N]_4H_2$ | III | 6 | $-0.463^d$ | 306 | 4.0 |
| $[SiW_{11}Fe(H_2O)O_{39}][(n-C_4H_9)_4N]_4H$ | IV | 5 | $-0.500$ | 224 | 3.7 |
| $[PW_{11}Fe(H_2O)O_{39}][(n-C_4H_9)_4N]_4$ | V | 4 | $-0.415$ | 197 | 5.0 |
| $[AsW_{11}Fe(H_2O)O_{39}][(n-C_4H_9)_4N]_4$ | V | 4 | $-0.317$ | 150 | 3.5 |
| $[BiW_{11}Fe(H_2O)O_{39}][(n-C_4H_9)_4N]_4H_2$ | III | 6 | NA | 95 | 2.5 |
| $[GeW_{11}Fe(H_2O)O_{39}][(n-C_4H_9)_4N]_4H$ | IV | 5 | $-0.267$ | 48 | (e) |
| $[SbW_{11}Fe(H_2O)O_{39}][(n-C_4H_9)N]_4H_2$ | III | 6 | $-0.217$ | 0 | |

[a] Air, 1500 psig, pressed on 60 g propane in 48 ml acetonitrile containing 0.023 mmoles catalyst. Heated to 125° C. with stirring for 20 hours. Product analysis by standardized glpc.
[b] Half Wave Potentials ($E_{1/2}$) determined in $CH_3CN(TBAPF_6)$ with acetate buffer (pH 4.7) vs. Ag/AgCl, $Fc/Fc^+$ = 283 mV.
[c] Acetone/isopropyl alcohol molar ratio.
[d] Estimate from very broad waves.
(e) No isopropyl alcohol detected.

TABLE II

EFFECT OF THE NUMBER OF $(n-C_4H_9)_4N$ GROUPS ON CATALYTIC ACTIVITY OF KEGGIN CATALYSTS

| CATALYST | $X^{(A)}$ A | Charge on Complex, Z | TO | ONE/ OL[B] |
|---|---|---|---|---|
| $[BiW_{11}Fe(H_2O)O_{39}][(n-C_4H_9)_4N]_3H_3$ | III | 6 | 248 | 3.2 |
| $[BiW_{11}Fe(H_2O)O_{39}][(n-C_4H_9)_4N]_4H_2$ | III | 6 | 95 | 2.5 |
| $[SbW_{11}Fe(H_2O)O_{39}][(n-C_4H_9)_4N]_3H_3$ | III | 6 | 144 | 3.5 |
| $[SbW_{11}Fe(H_2O)O_{39}][(n-C_4H_9)_4N]_4H_2$ | III | 6 | 0 | — |

[a] Air, 1500 psig, pressed on 60 g propane in 48 ml acetonitrile containing 0.023 mmoles catalyst. Heated to 125° C. with stirring for 20 hours. Product analysis by standardized glpc.
[B] Acetone/Isopropyl alcholol molar ratio.

TABLE III

EFFECT OF THE NATURE OF FRAMEWORK METAL ON OXIDATION ACTIVITY OF KEGGIN CATALYSTS

| CATALYST | $X^{(A)}$ A | Charge on Complex, Z | TO | ONE/ OL[b] |
|---|---|---|---|---|
| $[SiW_{11}Fe(H_2O)O_{39}][(n-C_4H_9)_4N]_4H$ | IV | 5 | 224 | 3.7 |
| $[SiMo_{11}Fe(H_2O)O_{39}][(n-C_4H_9)_4N]_4H$ | IV | 5 | 199 | 5.6 |
| $[PW_{11}Fe(H_2O)O_{39}][(n-C_4H_9)_4N]_4$ | V | 4 | 197 | 5.0 |
| $[PMo_{11}Fe(H_2O)O_{39}][(n-C_4H_9)_4N]_4$ | V | 4 | 171 | 4.5 |

[a] Air, 1500 psig, pressed on 60 g propane in 48 ml acetonitrile containing 0.023 mmoles catalyst. Heated to 125° C. with stirring for 20 hours. Product analysis by standardized glpc.
[b] Acetone/isopropyl alcohol molar ratio

The invention claimed is:

1. A method for oxidation of alkanes comprising contacting said alkane in the presence of air or oxygen with catalyst comprising polyoxoanion having the formula:

$$[H_{e-z}(R_4N)_z](XM_{11}M'O_{39})^{-e}$$

or $$[H_{e-z}(R_4N)_z](X_2M_{17}M'O_{61})^{-e}$$

wherein X comprises Group IIIB–VIB element; M comprises molybdenum, tungsten or vanadium or combinations thereof; M' is selected from the group consisting of ruthenium and first row transition metals substituted for a metal-oxygen (M=O) unit; R is an alkyl group comprising 1 to 8 carbon atoms; z is an integer from 1 to 7; e is an integer from 4 to 10; and e is the sum of number of tetraalkylammonium groups (z) and hydrogen atoms (e–z) needed to electronically balance the formula.

2. The method of claim 1 wherein R is butyl group.
3. The method of claim 1 wherein X is phosphorus.
4. The method of claim 1 wherein X is boron.
5. The method of claim 1 wherein X is silicon.
6. The method of claim 1 wherein X is arsenic.
7. The method of claim 1 wherein M is molybdenum.
8. The method of claim 1 wherein M is vanadium.
9. The method of claim 1 wherein M is tungsten.
10. The method of claim 1 wherein M' is iron, chromium or ruthenium.
11. The method of claim 10 wherein M' is iron.
12. The method of claim 10 wherein M' is ruthenium.
13. The method of claim 10 wherein M' is chromium.

14. The method of claim 1 wherein said oxidation is carried out in liquid phase at a temperature in the range of 50 to 200° C. and a pressure in the range of 0 to 5000 psig for 0.1 to 20 hours.

15. The method of claim 14 wherein said temperature is in the range of 50 to 150° C.

16. The method of claim 14 wherein said pressure is in the range of 15 to 1500 psig.

17. The method of claim 1 wherein said oxidation is carried out in vapor phase at a temperature in the range of 150 to 400° C., and a pressure in the range of 15 to 1200 psig.

18. The method of claim 17 wherein said pressure is in the range of 15 to 100 psig.

19. The method of claim 1 wherein said alkane contains 1 to 20 carbon atoms.

20. A method for oxidation of alkanes comprising contacting said alkane in the presence of air or oxygen with catalyst comprising a polyoxoanion comprising:

(a) a framework comprising 17 to 61 oxygen atoms (O) and 4 to 19 framework metal atoms (M) selected from the group consisting of molybdenum, tungsten and vanadium and combinations thereof;

(b) one or more atoms (M') selected from the group consisting of ruthenium and first row transition metalsr ruthenium substituted for one or more framework metal-oxygen units (M=O) in said framework;

(c) one or two central atoms (X) selected from the group consisting of Group IIIA–VIA elements of the Periodic Table; and (d) a sufficient number (e) of cations to electronically balance the charge (−e) of said polyoxoanion, wherein at least one of said cations comprises tetraalkylammonium cation.

* * * * *